(12) United States Patent
Reyes

(10) Patent No.: US 12,350,118 B2
(45) Date of Patent: Jul. 8, 2025

(54) DENTAL MIRROR CLEANER

(71) Applicant: Dental Holdings LLC, Vancouver, WA (US)

(72) Inventor: Hari Reyes, Ridgefield, WA (US)

( * ) Notice: Subject to any disclaimer, the term of this patent is extended or adjusted under 35 U.S.C. 154(b) by 447 days.

(21) Appl. No.: 17/726,191

(22) Filed: Apr. 21, 2022

(65) Prior Publication Data

US 2023/0106130 A1  Apr. 6, 2023

Related U.S. Application Data

(63) Continuation-in-part of application No. 17/495,484, filed on Oct. 6, 2021.

(51) Int. Cl.
*A61C 19/00* (2006.01)
*A61B 1/247* (2006.01)

(52) U.S. Cl.
CPC ............ *A61C 19/002* (2013.01); *A61B 1/247* (2013.01)

(58) Field of Classification Search
CPC ........ A61C 19/002; A61B 1/247; A61B 1/253
See application file for complete search history.

(56) References Cited

U.S. PATENT DOCUMENTS

| | | | | |
|---|---|---|---|---|
| 2,711,586 | A * | 6/1955 | Groves | A61C 1/08 433/95 |
| 2,984,009 | A * | 5/1961 | Codoni | A61B 1/253 433/30 |
| 3,032,879 | A * | 5/1962 | Lafitte | A61B 1/247 385/116 |
| 3,048,924 | A * | 8/1962 | Whitman | A61B 1/253 433/30 |
| 4,279,594 | A * | 7/1981 | Rigutto | A61B 1/253 433/95 |
| 2022/0386860 | A1* | 12/2022 | Ramot | A61B 1/253 |
| 2023/0105258 | A1* | 4/2023 | Reyes | A61B 1/015 433/31 |
| 2023/0107303 | A1* | 4/2023 | Banday | A61B 1/253 433/31 |

* cited by examiner

*Primary Examiner* — Edward Moran
*Assistant Examiner* — Matthew P Saunders
(74) *Attorney, Agent, or Firm* — Mark S Hubert

(57) ABSTRACT

A dental mirror cleaner that utilizes a spray of high pressure water and air at an angle across the reflective face of a dental mirror while in a patient's mouth to clean debris, blood and condensation from the mirror. It redirects the flow of the water and or air away from the centerline or linear axis of the mirror handle and sprays it offset from this centerline in a hemispherical pattern at an approximate 35 to 45 degree angle across the mirrored face.

6 Claims, 5 Drawing Sheets

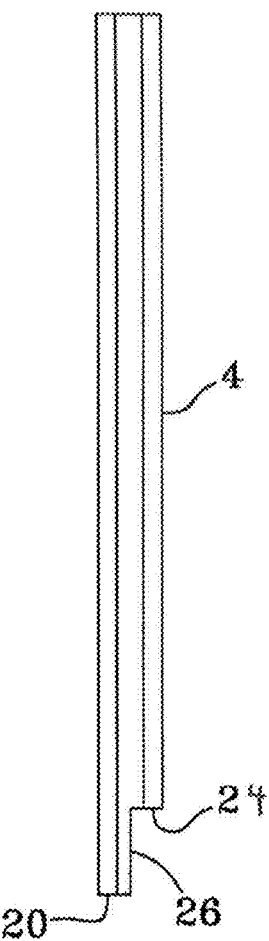
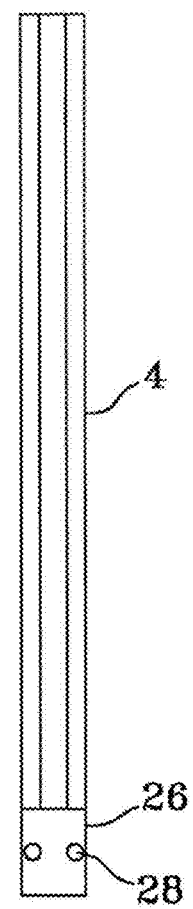
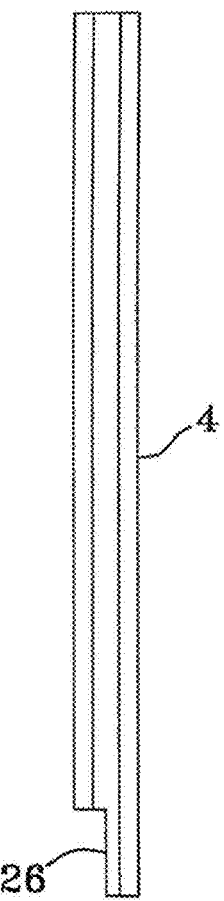
FIG. 5  FIG. 6  FIG. 7  FIG. 8
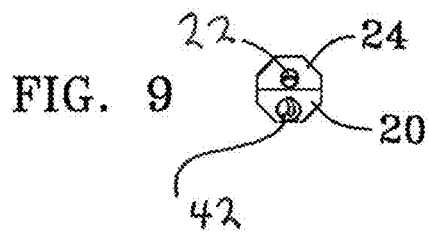

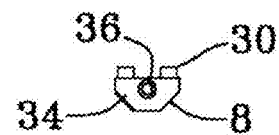
FIG. 10
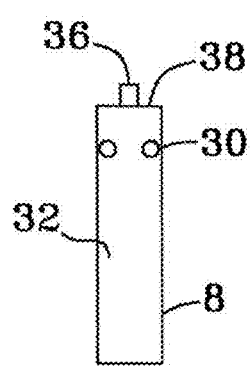 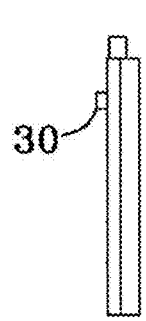  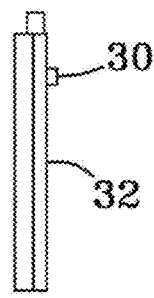
FIG. 11   FIG. 12   FIG. 13   FIG. 14
FIG. 15

DENTAL MIRROR CLEANER

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

CROSS-REFERENCE TO RELATED APPLICATIONS

Priority Claim to a Nonprovisional Application

This application is a continuation-in-part of U.S. patent application Ser. No. 17/495,484, filed Oct. 6, 2021, which is incorporated by reference herein in its entirety.

FIELD

The present disclosure relates, in general, to dentistry, and more particularly to the technology of cleaning of tools used in oral cavities.

BACKGROUND

When a dentist or dental technician performs work deep in a patient's mouth, generally an angled dental mirror is used. These have several inherent drawbacks. Blood, debris, water and fog accumulate on the top reflective face of the mirror. This causes the removal and cleaning of the mirror, the reinsertion and alignment of the mirror and the refocusing of the dentist's vision through his magnifying eyepiece. While certain substances on the mirror can remain somewhat unobtrusively on the mirror, other like blood, because of its quick coagulation time, cannot.

The dentist usually has a tool in both hands, such that a dirty mirror necessitates a dental assistant taking control of the mirror and cleaning it. If the mirror is only fogged with condensation, it still requires the dentist to momentarily stop work until the fog evaporates off of the mirror. All told, a dirty or fogged mirror costs the dentist hours of lost time each week. While a dental assistant can spray water and then air onto a mirror while the dentist works, it is very hard to precisely target the moving target of an angled mirror while in in a patient's mouth. Additionally, the dental assistant is usually handing the dentist tools at the same time.

Henceforth, a device that can clean debris, blood and condensation off of a dental mirror with pressurized water and or air while remaining in a patient's oral cavity would fulfill a long felt need in the dental industry. This new invention utilizes and combines known and new technologies in a unique and novel configuration to overcome the aforementioned problems and accomplish this.

BRIEF SUMMARY

In accordance with various embodiments, a dual seal dental mirror cleaner is provided.

In one aspect, a dental mirror cleaner that can spray pressurized water and/or air onto an angled dental mirror at the correct angle to completely clear the debris, blood or condensation off of the top reflective face of the mirror, is provided.

In another aspect, a dental mirror cleaner that has a sterilizable handle barrel and mirror, and a replaceable media spray diverter tube is provided.

In yet another aspect, a dental mirror cleaner that redirects the flow of pressurized water and air from the handle barrel into a media spray channel that sprays the mirror at the correct angle to completely clean debris, blood and condensation from the top face of the mirror.

Various modifications and additions can be made to the embodiments discussed without departing from the scope of the invention. For example, while the embodiments described above refer to particular features, the scope of this invention also includes embodiments having different combination of features and embodiments that do not include all of the above described features.

BRIEF DESCRIPTION OF THE DRAWINGS

A further understanding of the nature and advantages of particular embodiments may be realized by reference to the remaining portions of the specification and the drawings, in which like reference numerals are used to refer to similar components.

FIG. 4 is a proximal end view of the dental mirror cleaner;

FIGS. 5-8 are top, right side, bottom and left side views of the handle barrel;

FIG. 9 is a distal end view of the handle barrel;

FIG. 10 is a distal end view of the media spray diverter tube;

FIGS. 11-14 are top, right side, bottom and left side views of the media spray diverter tube; and FIG. 15 is a proximal end view of the media spray diverter tube.

DETAILED DESCRIPTION OF CERTAIN EMBODIMENTS

Reference will now be made in detail to embodiments of the inventive concept, examples of which are illustrated in the accompanying drawings. The accompanying drawings are not necessarily drawn to scale. In the following detailed description, numerous specific details are set forth to enable a thorough understanding of the inventive concept. It should be understood, however, that persons having ordinary skill in the art may practice the inventive concept without these specific details and that the described examples are provided for illustrative purposes and are not intended to limit the scope of the invention.

It will be understood that, although the terms first, second, distal and proximal, front and back, etc. may be used herein to describe various elements or sections thereof, these elements should not be limited by these terms. These terms are only used to distinguish one element or section thereof from another. For example, a first attachment could be termed a second attachment, and, similarly, a second attachment could be termed a first attachment, without departing from the scope of the inventive concept.

As used herein, the term "water and air spray syringe" refers to a device external to the dental mirror cleaner, that injects air and water into the handle barrel of the device to clean the mirror.

As used herein the term "handle barrel" refers to the structure that resides between the water and spray syringe and the diverter tube, channeling pressurized air and/or water to the media spray tube.

As used herein, the term "media" refers to the air, water and air/water combination that is provided by the water and air syringe to the dental mirror cleaner.

The present invention relates to a novel design for a dental mirror cleaner that functions to allow the dentist to clean the top face of his dental mirror with a water and air spray syringe while it remains in the oral cavity of the patient. The time savings for the dentist is expected to in the range of 15 minutes per patient.

Figure 1:
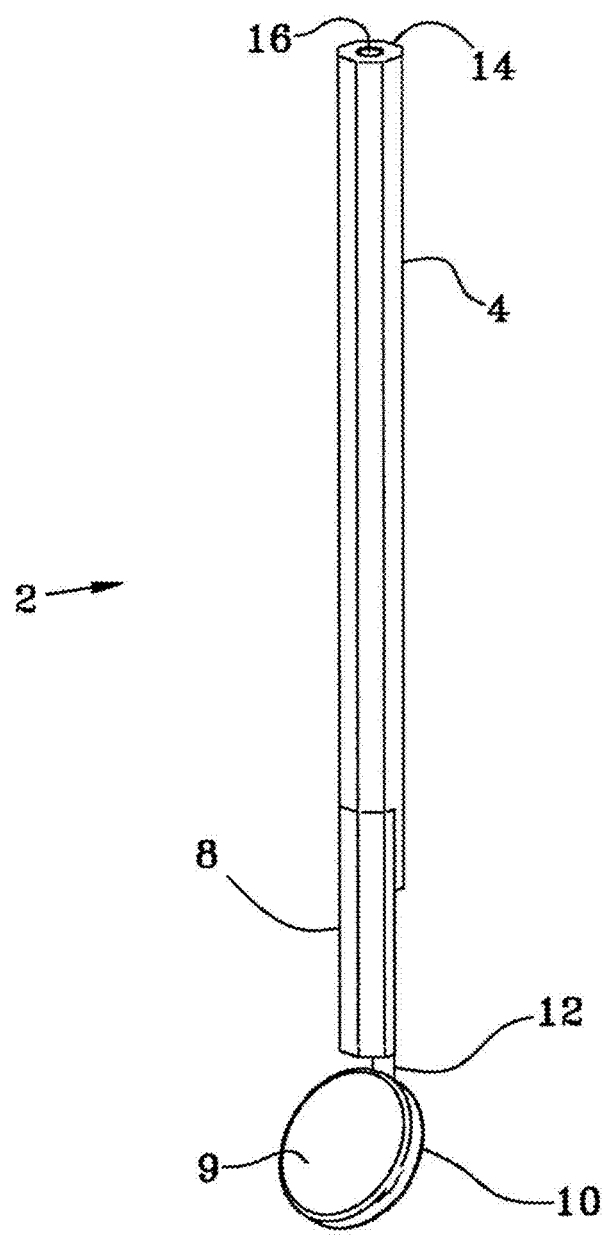
FIG. 1 is a front perspective view of the dental mirror cleaner.
Figure 2:
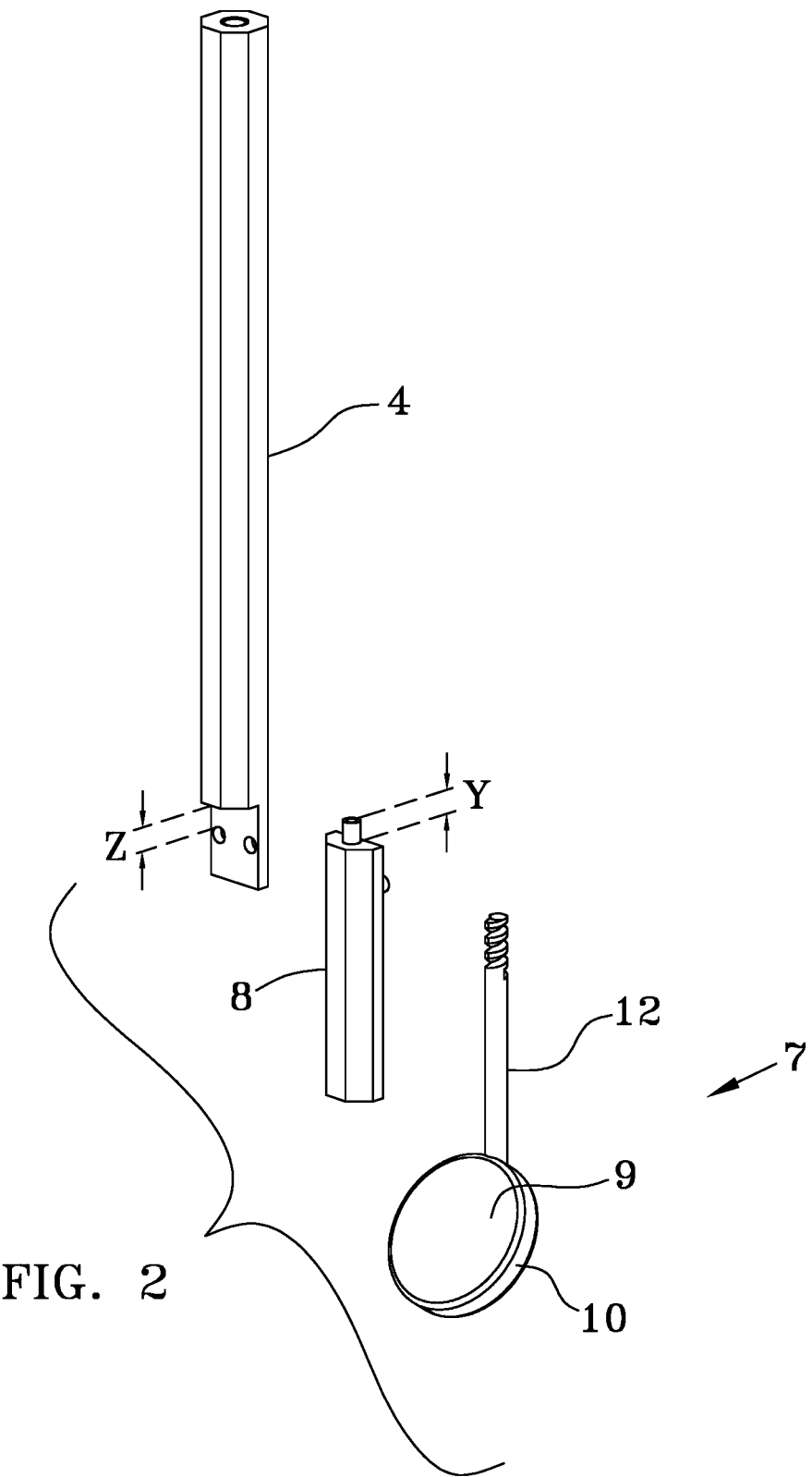
FIG. 2 is a perspective assembly view of the dental mirror cleaner.
Figure 3:
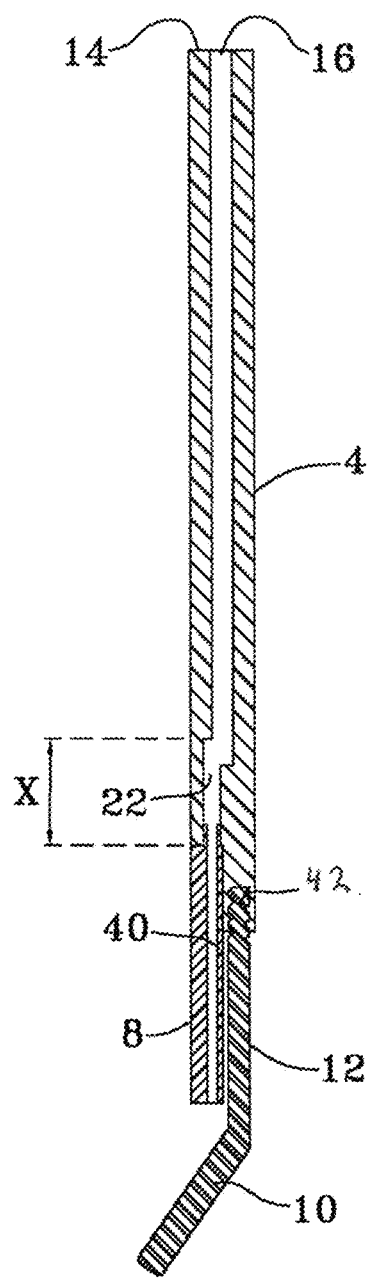
FIG. 3 is a side cross sectional view of the dental mirror cleaner.

Looking at FIGS. 1, 2 and 3 it can be seen that the dental mirror cleaner 2 consists of a sterilizable handle barrel 4, a replaceable media spray diverter tube 8 and an attachable mirror 7 having a circular mirrored disk 9 inset into a mirror body 10 coupled to an arm 12 extending therefrom the peripheral circular side of the mirror body 10. (In an alternate embodiment, the arm may extend from a back face of the mirror body 9.) The end of the arm 12 is affixed to the distal end of the handle barrel 4, preferably by threaded engagement. (In another alternate embodiment, the mirror and the barrel handle 4 may be formed as a single piece.)

In the preferred embodiment the mirror 7 is fabricated from stainless steel with a conventional mirrored disk 9 insert thereon, while in alternate embodiments, the mirrored disk 9 may be a highly polished stainless steel face. Onto the media inlet end 14 of the handle barrel 4, a conventional water and air spray syringe (not shown but well known in the art) may be attached so as to able to send its water and air down the internal media channel formed along the inside of the barrel handle 4.

The handle barrel 4 and the mirror body 10 can each be sterilized in an autoclave unit, while the media spray diverter tube 8 is made from a polymer, preferably polypropylene or a thermoplastic elastomer (TPE) and is intended to be replaced upon each use. It is a low cost consumable part.

The handle barrel 4 is a cylindrical, tubular member having a generally planar, media inlet end 14, (the proximal end) and a dual-stepped end (the distal end). This dual-stepped end has a planar media outlet face 24 and a planar mirror attachment face 20 that reside parallel to each other. (See FIGS. 4-9) Each of these faces 20 and 24 are approximately one half of the size of the top face of the media inlet end 14. Between these two faces 20 and 24 is an intermediary, vertical, planar face 26 that bisects the linear axis of the device 2 and resides perpendicularly to either of the faces 20 and 24. In this intermediary face 26 are two diverter tube locking sockets 28 that are frictionally engageable with the two diverter tube locking pegs 30. (See FIGS. 10-12 and 14-15) Although depicted as hexagonal in cross section, any cross sectional geometric configuration that is comfortable to hold such as circular, elliptical, octagonal or the equivalent, can be used for the handle barrel 4.

The internal media channel is a stepped channel made by the intersection of two separate offset bores, one from each end of the handle barrel 4. Neither bore extends to the opposite end of the barrel handle 4. The proximal bore 16 (preferably 4 mm in diameter) is formed beginning at the media inlet end 14 and is centered along the linear axis of the barrel handle 4. The distal bore 22 is formed from the media outlet face 24 of the dual stepped end 20 and resides parallel to the linear axis of the barrel handle 4. Its linear axis in no coincident with that of the proximal bore. These two bores, one from each end of the device 2 intersect at a distance from the media outlet face 24 as depicted by dimensional length arrow X. This offset in the media channel from the linear axis of the device 2 is responsible in keeping the thickness of the barrel handle 4 at a minimum for ergonomic reasons. The thickness of the barrel handle should approximate that of a pen or pencil.

The offset of the distal bore 22 from the barrel handle's centerline allows enough material at the distal end of the device 2 to secure the removeable mirror into a threaded bore 42 formed beginning at the mirror attachment face 20. This same offset of the distal bore 22 allows the air and water sprayed down the internal media channel to strike the trailing, upper edge of the mirrored disk 9 at the appropriate angle to efficiently clear blood, saliva and fog off of it.

The replaceable media spray diverter tube 8 is configured the same as a linear half section of the barrel handle 4. It has a planar inner face 32 with a pair of cylindrical locking pegs 30 extending normally therefrom. It also has a cylindrical media plug 36 extending from its planar top inlet face 34. There is a media outlet through-bore 40 extending from the center of the media plug 36, along the length of its body and out the bottom, discharge face of the diverter tube 8. The planar top face and bottom discharge face are parallel with the inner face The length of this media plug 36 has a length depicted by dimensional arrow Y that is less that X. This ensures that the planar top face 34 of the diverter tube 8 seats completely against the bottom face of the media outlet face 24 so as to prevent media leakage while the media plug 36 does not extend up into the interface of the proximal bore 16 and distal bore 22 so as to block flow. The distance between the media outlet face 24 and the top of the locking pegs 30, depicted by dimensional arrow Z is greater than or equal to the height Y of the media plug 36. With Z greater than Y there is an upward pressure on both of the seals formed between the barrel handle 4 and the diverter tube 8.

For assembly, the mirror arm 12 is threadingly engaged into the threaded bore 42. The diverter tube 8 is tipped so that the top narrow end of its tapered media plug 36 enters the distal bore 22 and it is inserted fully until the top face 34 of the diverter tube 8 abuts the planar media outlet face 24 of the dual stepped distal end of the barrel handle 4. The diverter tube 8 is then urged sideways until its two locking pegs 30 are frictionally engaged into the diverter tube locking sockets 28. These locking pegs 30 act to ensure that there is no movement of the diverter tube 8 with respect to the handle barrel 4 and the seal made by the tapered media plug 36 and the distal bore 22, and the seal made by the top face 34 of the diverter tube 8 and the media outlet face 24 remain intact.

This media plug 36 may be configured as a straight cylinder however preferably, it is tapered so as to be slightly narrower at its top end, for ease of entry into the distal bore 22.

When engaged, the handle barrel 4 and the diverter tube 8 are connected in a leak proof manner with dual seals, that are able to withstand the approximate 80 psi pressure generated by the water and air spray syringe. The locking pegs 30 and locking sockets 28 similarly, may be tapered for ease of connection and to enhance the seal caused by their frictional engagement. Preferably the media spray tube 8 is made of a polymer with a Durometer Shore A Hardness Scale of 80 to allow the slight elastic deformation of the pegs 30 under compression while connecting the two components.

In operation, a water and air syringe device may be removably coupled to the media inlet end 14. This is a device commonly found in all dental offices and capable of spraying media (water, air or a water and air mixture). When operatively coupled to the media inlet end, it allows the user to spray media down the internal media channel through the proximal bore 16, the distal bore 22 and the media outlet bore 40 so as to spray across the face of the angled mirrored disk 9 at the preferred 35 to 45 degree angle, and keep the mirror clear for the dentist. Thus, there is a 35 to 45 degree angle between the top face of the mirror and the linear axis of the media outlet bore. This quick cleaning eliminates the need to remove the mirror from the patient's mouth and the need for a dentist to have to refocus their eyes to begin work again. This device eliminates the need for a dental assistant to aid the dentist in keeping the mirror clean. Conservative studies show that this device 2 should be able to save approximately 15 minutes per patient. The dual seal ensures that the high pressure water and or air does not leak out of the device.

When the diverter tube 8 is coupled to the handle barrel 4 the media channel is in fluid communication with, the media outlet bore 40 along the entire device 2. This offset redirection of the media stream is necessary to have the media strike the angled mirror at the preferred angle to quickly clean and clear the mirror 10.

The media spray diverter tube 8 may be made of a polymer and be a consumable part of the device 2 while the handle barrel 4, the mirror 10 and mirror arm 12 are made of an autoclavable material, preferably stainless or a plated steel.

While certain features and aspects have been described with respect to exemplary embodiments, one skilled in the art will recognize that numerous modifications are possible. Device components described according to a particular structural architecture may be organized in alternative structural architectures and/or incorporated within other described devices. Hence, while various embodiments are described with—or without—certain features for ease of description and to illustrate exemplary aspects of those embodiments, the various components and/or features described herein with respect to a particular embodiment can be substituted, added, and/or subtracted from among other described embodiments, unless the context dictates otherwise. It will be appreciated that the invention is intended to cover all modifications and equivalents within the scope of the following claims.

Having thus described the invention, what is claimed as new and desired to be secured by Letters Patent is as follows:

The invention claimed is:

1. A dental mirror cleaning device, comprising:
 a barrel handle having a proximal, media inlet end and a distal, media outlet end and a linear axis;
 a mirror affixed to said media outlet end;
 a proximal bore formed in said barrel handle, from said media inlet end, and residing along said linear axis of said barrel handle;
 a distal bore formed in said barrel handle, from said media outlet end, and residing parallel to said linear axis of said barrel handle;
 a media spray diverter tube frictionally engaged with said barrel handle at said media outlet end, said media spray diverter tube having a planar top inlet face, a bottom discharge face and a planar inner face perpendicular to said top face and said bottom discharge face;
 a media outlet through-bore formed through said media spray diverter tube between said top inlet face and said bottom discharge face;
 wherein said distal bore and said proximal bore have an intersection, but have offset, parallel axes that are non-colinear;
 at least one media spray diverter tube locking peg;
 at least one media spray diverter tube locking socket;
 and wherein said distal bore, said proximal bore and said media outlet through-bore form a non-linear fluid passage between said media inlet end of said barrel handle and said bottom discharge face of said media spray diverter tube.

2. The dental mirror cleaning device of claim 1, further comprising:
 a dual stepped configuration formed on said distal media outlet end of said barrel handle having a planar media outlet face, a parallel planar mirror attachment face, and an intermediary, vertical, planar face that bisects said linear axis of said dental mirror cleaning device and resides perpendicularly to said media outlet face and said mirror attachment face;
 a cylindrical media plug extending from said top inlet face of said media spray diverter tube, with said media outlet through-bore passing through a center of said cylindrical media plug, wherein said cylindrical media plug is frictionally engaged with said proximal bore to form a first seal, and wherein said planar top inlet face of said media spray diverter tube contacts said of said media outlet face of said barrel handle to form a second seal;
 said at least one media spray diverter tube locking peg extending normally from said inner face of said media spray diverter tube;
 said at least one media spray diverter tube locking socket formed in said intermediary face wherein said at least one locking socket is frictionally engaged with said at least one media spray diverter tube locking peg.

3. The dental mirror cleaning device of claim 2, wherein said cylindrical media plug is a tapered cylinder and said at least one media spray diverter tube locking peg is a tapered cylinder.

4. The dental mirror cleaning device of claim 3, wherein said media spray diverter tube is made of a polymer having a score of 80 on the Durometer Shore A Hardness Scale to allow the slight elastic deformation of the pegs 30 under compression.

5. The dental mirror cleaning device of claim 3, further comprising: a length X between said intersection of said distal bore and said proximal bore and said media outlet face; a length Y of said cylindrical media plug; a length Z between said media outlet face and a top of said at least one media spray diverter tube locking peg; wherein Y is less than X; and wherein Z is greater than or equal to Y.

6. The dental mirror cleaning device of claim 5, wherein said mirror resides at a 35 to 45 degree angle relative to a linear axis of said media outlet through-bore.

* * * * *